US011707508B2

United States Patent
Zalutskaya et al.

(10) Patent No.: US 11,707,508 B2
(45) Date of Patent: Jul. 25, 2023

(54) ANTI-RETROVIRAL TREATMENT USING GROWTH HORMONE

(71) Applicants: ARES TRADING S.A., Aubonne (CH); Nicolas Chomont, Montreal (CA); Jean-Pierre Routy, Westmount (CA)

(72) Inventors: Alena Zalutskaya, Jamaica Plain, MA (US); John Gourley, Plainville, MA (US); Nicolas Chomont, Montreal (CA); Jean-Pierre Routy, Westmount (CA); Steven Deeks, San Francisco, CA (US)

(73) Assignee: ARES TRADING S.A., Aubonne (CH)

( * ) Notice: Subject to any disclaimer, the term of this patent is extended or adjusted under 35 U.S.C. 154(b) by 39 days.

(21) Appl. No.: 16/679,425

(22) Filed: Nov. 11, 2019

(65) Prior Publication Data
US 2020/0061159 A1   Feb. 27, 2020

Related U.S. Application Data

(63) Continuation of application No. 15/867,829, filed on Jan. 11, 2018, now abandoned.

(60) Provisional application No. 62/445,501, filed on Jan. 12, 2017.

(51) Int. Cl.
| | |
|---|---|
| *A61K 38/27* | (2006.01) |
| *A61P 31/18* | (2006.01) |
| *A61K 31/52* | (2006.01) |
| *A61K 31/708* | (2006.01) |
| *A61K 31/7068* | (2006.01) |
| *A61K 31/341* | (2006.01) |
| *A61K 31/675* | (2006.01) |
| *A61K 31/496* | (2006.01) |
| *A61K 31/536* | (2006.01) |
| *A61K 31/505* | (2006.01) |
| *A61K 31/551* | (2006.01) |
| *A61K 31/7072* | (2006.01) |

(52) U.S. Cl.
CPC ............ *A61K 38/27* (2013.01); *A61K 31/341* (2013.01); *A61K 31/496* (2013.01); *A61K 31/505* (2013.01); *A61K 31/52* (2013.01); *A61K 31/536* (2013.01); *A61K 31/551* (2013.01); *A61K 31/675* (2013.01); *A61K 31/708* (2013.01); *A61K 31/7068* (2013.01); *A61K 31/7072* (2013.01); *A61P 31/18* (2018.01)

(58) Field of Classification Search
None
See application file for complete search history.

(56) References Cited

PUBLICATIONS

Chomont, N. et al. "HIV reservoir size and persistence are driven by T cell survival and homeostatic proliferation" *Nature Medicine*, Aug. 2009, pp. 893-900 and Online Methods p. 1, vol. 15, No. 8.
Chun, T.-W. et al. "Presence of an inducible HIV-1 latent reservoir during highly active antiretroviral therapy" *Proceedings of the National Academy of Sciences*, Nov. 1997, pp. 13193-13197, vol. 94.
Durand, C. M. et al. "Developing strategies for HIV-1 eradication" *Trends in Immunology*, Nov. 2012, pp. 554-562, vol. 33, No. 11.
Finzi, D. et al. "Identification of a Reservoir for HIV-1 in Patients on Highly Active Antiretroviral Therapy" *Science*, Nov. 14, 1997, pp. 1295-1300, vol. 278.
Herasimtschuk, A. A. et al. "Effects of recombinant human growth hormone on HIV-1-specific T-cell responses; thymic output and proviral DNA in patients on HAART: 48-week follow-up" *Journal of Immune Based Therapies and Vaccines*, Oct. 31, 2008, pp. 1-13. vol. 6, No. 7.
Herasimtschuk, A. A. et al. "Low-dose growth hormone for 40 weeks induces HIV-1-specific T cell responses in patients on effective combination anti-retroviral therapy" *Clinical and Experimental Immunology*, pp. 444-453, vol. 173.
Lo, J. C. et al. "The Effects of Recombinant Human Growth Hormone on Body Composition and Glucose Metabolism in HIV-Infected Patients with Fat Accumulation" *The Journal of Clinical Endocrinology & Metabolism*, Aug. 2001, pp. 3480-3487, vol. 86, No. 8.
Lo, J. C. et al. "The Effects of Low-Dose Growth Hormone in HIV-Infected Men with Fat Accumulation: A Pilot Study" *HIV/AIDS*, Sep. 1, 2004, pp. 732-735, vol. 39.
Napolitano, L. A. et al. "Increased thymic mass and circulating naive CD4 T cells in HIV-1-infected adults treated with growth hormone" *AIDS*, 2002, pp. 1103-1111, vol. 16.
Napolitano, L. A. et al. "Growth hormone enhances thymic function in HIV-1-infected adults" *The Journal of Clinical Investigation*, Mar. 2008, pp. 1085-1098, vol. 118, No. 3.
Plana, M. et al. "The reconstitution of the thymus in immunosuppressed individuals restores CD4-specific cellular and humoral immune responses" *Immunology*, 2011, pp. 318-328, vol. 133.

(Continued)

*Primary Examiner* — Julie Ha
*Assistant Examiner* — Tara L Martinez
(74) *Attorney, Agent, or Firm* — Saliwanchik, Lloyd & Eisenschenk

(57) ABSTRACT

The subject invention pertains to methods of treating HIV-1 infected subject comprising the administration of growth hormone to a subject infected by HIV-1. The subject may be undergoing co-administration of anti-retroviral therapies (ARTs), may be untreated with anti-retroviral drugs (ARDs) or may be in a period of time where no ART is being administered. Growth hormone may be administered at a fixed dosage for a set period of time or may be administered at a first dosage for a first period of time that may then be increased or decreased to a second dosage for a second period of time.

17 Claims, No Drawings

Specification includes a Sequence Listing.

(56) References Cited

PUBLICATIONS

Procopio, F. A. et al. "A Novel Assay to Measure the Magnitude of the Inducible Viral Reservoir in HIV-infected Individuals" *EBioMedicine*, 2015, pp. 874-883, vol. 2.

Siliciano, J. D. et al. "Long-term follow-up studies confirm the stability of the latent reservoir for HIV-1 in resting $CD4^+$ T cells" *Nature Medicine*, Jun. 2003, pp. 727-728, vol. 9, No. 6.

Spivak, A. M. et al. "A Pilot Study Assessing the Safety and Latency-Reversing Activity of Disulfiram in HIV-1-Infected Adults on Antiretroviral Therapy" *HIV/AIDS*, Mar. 15, 2014, pp. 883-890, vol. 58.

Wightman, F. et al. "Both $CD31^+$ and $CD31^-$ Naive $CD4^+$ T Cells Are Persistent HIV Type 1-Infected Reservoirs in Individuals Receiving Antiretroviral Therapy" *The Journal of Infectious Diseases*, Dec. 1, 2010, pp. 1738-1748, vol. 202, No. 10.

Wong, J. K. et al. "Recovery of Replication-Competent HIV Despite Prolonged Suppression of Plasma Viremia" *Science*, Nov. 14, 1997, pp. 1291-1295, vol. 278.

Health Canada [online], Clinical trial information, retrieved on Jan. 24, 2017, retrieved from the internet, URL: https://health-products.canada.ca/ctdb-bdec/search-recherche.do;jsessionid=503AE52C9ABF2B5959A08456521058B6, "A Proof-of-concept study to assess the effect of recombinant human growth hormone on the size of the replication-competent viral reservoir in HIV-infected individuals on suppressive antiretroviral therapy" pp. 1-3; Protocol No. MS700149_0002.

Information and Consent Form, "A Proof-of-concept study to assess the effect of recombinant human growth hormone on the size of the replication-competent viral reservoir in HIV-infected individuals on suppressive antiretroviral therapy" McGill University Health Centre, Protocol No. MS700149_0002, MUHC Study Code: 2017-2835, Oct. 13, 2016, pp. 1-15.

"A Proof-of-concept study to assess the effect of recombinant human growth hormone on the size of the replication-competent viral reservoir in HIV-infected individuals on suppressive antiretroviral therapy" Protocol No. MS700149_0002, Aug. 22, 2016, pp. 1-48.

Atta, M. G. et al. "Clinical Pharmacology in HIV Therapy" *Clinical Journal of the American Society of Nephrology*, Apr. 2018, pp. 1-10, vol. 14.

AIDSinfo, "Guidelines for the Use of Antiretroviral Agents in Adults and Adolescents Living with HIV", Apr. 8, 2015, pp. 1-2.

Boer, H. et al. "Guidelines for optimizing growth hormone replacement therapy in adults" *Horm. Res.* 1997, pp. 21-30.

ANTI-RETROVIRAL TREATMENT USING GROWTH HORMONE

CROSS-REFERENCE TO A RELATED APPLICATIONS

This application is a continuation of U.S. application Ser. No. 15/867,829, filed Jan. 11, 2018, which claims the benefit of U.S. Provisional Application Ser. No. 62/445,501, filed Jan. 12, 2017, the disclosures of which are hereby incorporated by reference in their entirety, including all figures, tables and amino acid or nucleic acid sequences.

The Sequence Listing for this application is labeled "Seq-List.txt" which was created on Jan. 5, 2018 and is 2 KB. The entire content of the sequence listing is incorporated herein by reference in its entirety.

BACKGROUND OF THE INVENTION

Anti-retroviral therapy (ART) with anti-retroviral drugs (ARD) has dramatically reduced the death rate from AIDS and improved the quality of life of many HIV-infected individuals [1]. A sterilizing cure, in which the virus is completely eradicated, would require the elimination of all replication-competent viruses throughout the body. An alternative approach provides for providing an individual with good long-term health in the absence of ART, or a disease "remission". Such a "remission" may be achieved by reducing the amount of residual HIV during ART (the "viral reservoir") to levels which the immune system can effectively control [3]. This is commonly referred to as a "functional cure" in which the viral reservoir is naturally controlled by the host. Both forms of cure (sterilizing and functional) would require eliminating, or at least reducing, the reservoirs of HIV infection. Several strategies aimed at reducing the size of the viral reservoir have been tested within the past 5 years. Among them, the "shock and kill" approach consists in forcing viral gene expression in order to flush out the latent reservoir. Disappointingly, none of these interventions to date have had a demonstrable effect on the size of the latent HIV reservoir. Thus, novel strategies are needed in order to improve the reduction of the latent HIV reservoir size.

BRIEF SUMMARY OF THE INVENTION

One aspect of the present invention relates to the treatment of HIV-infected individuals with growth hormone (GH) (the use of GH for the treatment of HIV-infected individuals). In certain embodiments of this aspect of the invention, the HIV-infected individuals are undergoing concomitant ART (simultaneous treatment with anti-retroviral drugs) (ARD). The present invention also provides other aspects that provide various GH dosing regimens suitable for the treatment of HIV-infected individuals.

Another aspect of the invention is directed to the use of growth hormone for the reduction of latent HIV reservoir size in HIV-infected individuals (e.g., the use of GH to reduce the latent HIV reservoir size in HIV-infected individuals). Thus, methods of treating HIV-infected individuals with growth hormone in amounts effective to reduce the latent HIV reservoir within the treated individual are provided. While the treatment is contemplated for use in all HIV-infected populations, certain populations may be excluded from treatment within the context of the present invention. For example, individuals receiving growth hormone treatment for HIV-associated wasting (cachexia) can be excluded from the patient population being treated with growth hormone.

DETAILED DISCLOSURE OF THE INVENTION

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed. In the context of compositions containing amounts of GH where the terms "about" or "approximately" are used, these compositions contain the stated amount of the ingredient with a variation (error range) of 0-10% around the value (X±10%). When used in the context of time (e.g., days or weeks), the terms "about" or "approximately" provide for variations of up to 5 days.

The term "growth hormone (GH)", as used herein, is intended to include growth hormone from various sources. In particular embodiments, the GH is human origin (for example, isolated from biological fluids or obtained by DNA recombinant techniques from prokaryotic or eukaryotic host cells. In a particularly preferred embodiment, GH that is administered in accordance with the disclosed methods is SEROSTIM® and/or SAIZEN®. SAIZEN and SEROSTIM are somatropin, a recombinant human growth hormone (rhGH) produced by genetically engineered mammalian cells (mouse C127). Somatropin is a single-chain, non-glycosylated protein of 191 amino acids with two disulfide bridges. Of course other recombinant growth hormones can be used in accordance with the claimed invention and non-limiting examples of such recombinant growth hormones include NUTROPIN (Genentech), HUMATROPE (Lilly), GENOTROPIN (Pfizer), NORDITROPIN (Novo), and OMNITROPE (Sandoz). Within the context of this application, GH can be administered systemically, and preferably subcutaneously or intramuscularly. Intradermal, transdermal (e.g. in slow release formulations), intravenous, oral, topical, rectal, and intranasal routes of administering GH to a subject are also contemplated.

The terms "co-administration," "administered in combination with," and their grammatical equivalents encompass administration of two or more agents to a subject so that both agents and/or their metabolites are present in the subject at the same time. Co-administration includes simultaneous administration in separate compositions, administration at different times in separate compositions, or administration in a composition in which both agents are present.

"Subject" refers to an animal, such as a mammal, for example a human. The methods described herein can be useful in both pre-clinical human therapeutics and veterinary applications. In some embodiments, the subject is a mammal (such as a primate model of disease), and in some embodiments, the subject is human. The terms "subject", "individual" and "patient" can be used interchangeably.

The terms "simultaneous" or "simultaneously" as applied to administering agents to a subject refer to administering one or more agents at the same time, or at two different time points that are separated by no more than 1 hour. The term "sequentially" refers to administering more than one agent at two different time points that are separated by more than 1 hour, e.g., about 2 hours, about 5 hours, 8 hours, 1 day, 2 days, 3 days, 4 days, 5 days, 6 days, 7 days or even longer.

ARD that can be used in ART are identified in Table 1. ART may be administered to an individual treated in accordance with the claimed invention for a period of time prior to treatment with growth hormone in amounts sufficient to reduce the latent HIV reservoir within the subject. In certain embodiments, the HIV-infected individual is treated with ART for a period of at least 6 months, at least 12 months, at least 18 months or at least 24 months prior to treatment with growth hormone as disclosed herein. The terms "individual", "subject" and HIV-1 infected individual" (and grammatical variants thereof) can be used interchangeably within this disclosure.

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. A range can be denoted numerically (e.g., 0.1-1.0) or by the use of the phrase "up to" (e.g., up to 5 days). Where the phrase "up to" is used, the term includes, as a lower limit, the value of 0 (zero).

"A week" refers to a period of time of about 5, about 6 or about 7 days. "A month" refers to a period of time of about 28, about 29, about 30 or about 31 days.

As discussed above, one aspect of the present invention is directed to the use of growth hormone for the treatment of HIV-infected individuals. In certain embodiments of this aspect of the invention, a reduction of latent HIV reservoir size in HIV-infected individuals may also be observed in HIV-infected individuals undergoing treatment according to the regimens provided herein. Thus, HIV-infected individuals can be treated with growth hormone in amounts sufficient to reduce the latent HIV reservoir within the individual. Individuals who are to be treated in the context of this invention may be undergoing concomitant (simultaneous) anti-retroviral therapy (ART), may be untreated (no previous treatment with ARDs) or may be in a period of time during which ART is not, presently, being administered (an "ART-free period").

While a HIV-infected individual can be treated in an ongoing manner with growth hormone, certain embodiments provide for limiting the time the subject is treated. For example the subject can be treated for a total of about 52 weeks, about 48 weeks, about 44 weeks, about 40 weeks, about 36 weeks, about 32 weeks, about 28 weeks, about 24 weeks, about 20 weeks, about 16 weeks, about 12 weeks, about 8 weeks or about 4 weeks. Treatment can be suspended for a period of time, for example a period of about 4 weeks to about 52 weeks and then re-initiated at the same dose of GH, and increased dose of GH or a reduced dose of GH. The GH dose can range between about 1 mg/day to about 5 mg/day and, in preferred embodiments will be about 3 mg/day (30-40 µg/kg/d). Certain aspects of the invention provide a dosing regimen that utilizes two or more different dosages of growth hormone for two or more different periods of time.

One such dosing regimen provides for the administration of growth hormone to an HIV-infected individual in an amount of about 2 mg/day to about 5 mg/day for a period of about 24 weeks followed by a dose reduction to between about 1 mg/day to about 4 mg/day. In certain preferred embodiments, the HIV-infected individual is treated with an initial dose of about 3 mg/day followed by a reduced dose of about 1.5 mg/day. In an even more preferred embodiment, the HIV-infected individual is treated with an initial dose of about 3 mg/day for a period of about 24 weeks followed by a treatment with a reduced dose of about 1.5 mg/day for a period of about 24 weeks.

Another dosing regimen provides for the administration of growth hormone to an HIV-infected individual in an amount of about 2 mg/day to about 5 mg/day for a period of about 2 to 52 weeks followed by a dose reduction to between about 1 mg/day to about 4 mg/day for a period of about 2 to about 52 weeks. In certain preferred embodiments, the HIV-infected individual is treated with an initial dose of about 3 mg/day followed by a reduced dose of about 1.5 mg/day. In an even more preferred embodiment, the HIV-infected individual is treated with an initial dose of about 3 mg/day for a period of about 20 weeks to about 30 weeks followed by a treatment with a reduced dose of about 1.5 mg/day for a period of about 20 weeks to about 30 weeks.

The terms "dose reduction" or "reduced dose" mean that the amounts administered within the second period of time is reduced as compared to the amount of growth hormone administered during the first period of time. The dose reduction can be between at least 20% and 80%. Thus, if the HIV-infected individual is treated with an initial dose of 5 mg/day, the reduced dose administered in the second period of time could be between 1 mg/day and 4 mg/day. As would be apparent, the reduced dose administered during the second time period is always less than the dose administered during the first period of time.

The terms "dose increase" or "increased dose" mean that the amounts administered within the second period of time is increased as compared to the amount of growth hormone administered during the first period of time. The dose increase can be between at least 1.5× and 5×. Thus, if the HIV-infected individual is treated with an initial dose of 5 mg/day, the increased dose administered in the second period of time could be between 7.5 mg/day and 25 mg/day. As would be apparent, the increased dose administered during the second time period is always greater than the dose administered during the first period of time.

One such dosing regimen provides for the administration of growth hormone to an HIV-infected individual in an amount of about 2 mg/day to about 5 mg/day for a period of about 24 weeks followed by a dose increase to between about 3 mg/day to about 25 mg/day. In certain preferred embodiments, the HIV-infected individual is treated with an initial dose of about 3 mg/day followed by an increased dose of about 5 mg/day. In an even more preferred embodiment, the HIV-infected individual is treated with an initial dose of about 3 mg/day for a period of about 24 weeks followed by a treatment with an increased dose of about 5 mg/day for a period of about 24 weeks.

Another dosing regimen provides for the administration of growth hormone to an HIV-infected individual in an amount of about 2 mg/day to about 5 mg/day for a period of about 2 to 52 weeks followed by a dose increase to between about 3.5 mg/day to about 25 mg/day for a period of about 2 to about 52 weeks. In certain preferred embodiments, the HIV-infected individual is treated with an initial dose of about 3 mg/day followed by an increased dose of about 15 mg/day. In an even more preferred embodiment, the HIV-infected individual is treated with an initial dose of about 3 mg/day for a period of about 20 weeks to about 30 weeks followed by a treatment with an increased dose of about 5 mg/day for a period of about 20 weeks to about 30 weeks.

HIV-infected individuals who can be treated within the context of this invention include those with both detectable and undetectable HIV-1 RNA levels. In preferred embodiments, subjects with HIV-1 RNA levels below the limit of quantification using an FDA-approved assay for a period of at least 6 month, at least 12 months, at least 18 months or at least 24 months prior the initiation of the growth hormone treatment are treated in accordance with the disclosed methods. Table 2 identified currently FDA-approved assays.

As discussed above, the present invention provides methods of reducing the latent HIV reservoir in an HIV-infected individual. Thus, the disclosed invention can further comprise testing treated individuals to determine the level of the HIV reservoir before and/or after treatment with GH. The size of the replication competent HIV reservoir can be measured by any means known in the art. For example, a quantitative viral outgrowth assay (mQVOA) can be used to measure the competent HIV reservoir in an individual at the onset of treatment or prior to the onset of treatment and at later times during the treatment regimen (for example, after 24 and 48 weeks of treatment with recombinant human growth hormone). Other markers of viral persistence (HIV DNA and TILDA) can also be measured according to methods known in the art.

The treatment regimens disclosed also provides certain embodiments varying the length of time that the subject is treated. For example the subject can be treated for a total of about 52 weeks, about 48 weeks, about 44 weeks, about 40 weeks, about 36 weeks, about 32 weeks, about 28 weeks, about 24 weeks, about 20 weeks, about 16 weeks, about 12 weeks, about 8 weeks or about 4 weeks. As discussed above, certain aspects of the invention provide a dosing regimen that utilizes two or more different dosages of growth hormone for two or more different periods of time.

TABLE 1

| Anti-Retroviral Drugs |
| --- |
| Nucleoside/Nucleotide Analogues |
| Abacavir |
| Didanosine |
| Emtricitabine |
| Lamivudine |
| Stavudine |
| Tenofovir disoproxil fumarate |
| Tenofovir alafenamide |
| Zalcitabine |
| Zidovudine |
| Nonnucleoside Reverse Transcriptase Inhibitors |
| Delavirdine |
| Efavirenz |
| Etravirine |
| Nevirapine |
| Rilpivirine |
| Protease Inhibitors |
| Amprenavir |
| Atazanavir |
| Darunavir |
| Fosamprenavir |
| Indinavir |
| Lopinavir/Ritonavir |
| Nelfinavir |
| Ritonavir |
| Saquinavir |
| Tipranavir |
| Fusion Inhibitors |
| Enfuvirtide |
| Chemokine Coreceptor Antagonists |
| Maraviroc |
| Integrase Inhibitors |
| Dolutegravir |
| Elvitegravir |
| Raltegravir |
| Pharmacokinetic Enhancers |
| Cobicistat |

TABLE 2

FDA-Approved Quantitative HIV-1 RNA Assays for Viral Load Monitoring

| Test Name | Manufacturer | Method | Lower LOQ (copies/mL) | Upper LOQ (copies/mL) |
| --- | --- | --- | --- | --- |
| Abbott RealTime HIV-1 | Abbott Laboratories | Real-time PCR | 40* | 10,000,000 |
| Cobas AmpliPrep/Cobas TaqMan HIV-1 Test, version 2.0 | Roche Diagnostics | Real-time PCR | 20 | 10,000,000 |
| Cobas HIV-1 quantitative NAT for use on Cobas 6800/8800 systems | Roche Diagnostics | Real-time PCR | 20 | 10,000,000 |
| Cobas TaqMan HIV-1 Test, v2.0 For Use With The High Pure System | Roche Diagnostics | Real-time PCR | 34 | 10,000,000 |

LOQ, limit of quantification.
*This lower LOQ applies when 1.0 mL of plasma is used. When 0.5 mL and 0.2 mL of plasma are used, the lower LOQ is 75 copies/mL and 150 copies/mL, respectively.

All patents, patent applications, provisional applications, and publications referred to or cited herein are incorporated by reference in their entirety, including all figures and tables, to the extent they are not inconsistent with the explicit teachings of this specification. Following are examples which illustrate procedures for practicing the invention.

These examples should not be construed as limiting. All percentages are by weight and all solvent mixture proportions are by volume unless otherwise noted. It should also be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

Example 1—HIV-1 Treatment Protocol

HIV-1-infected adults will be enrolled in a prospective, open-label, single-arm study of recombinant human growth hormone treatment. Participants will be treated with recombinant human growth hormone for a total of 48 weeks.

The initial recombinant human growth hormone dose will be 3 mg/day (30-40 μg/kg/d) for 24 weeks administered by subcutaneous injection on an outpatient basis, followed by dose reduction to 1.5 mg/day for the final 24 weeks of the treatment period, also conducted on an outpatient basis. Participants will be instructed to subcutaneously inject recombinant human growth hormone between 7 and 10 p.m., daily.

The size of the replication competent reservoir will be measured by a modified version of the quantitative viral outgrowth assay (mQVOA) at baseline (two measurements prior to the start of treatment with GH), and after 24 and 48 weeks of treatment with recombinant human growth hormone. Other markers of viral persistence (HIV DNA and TILDA) will be measured at various time points during the course of the study.

1. Primary Endpoint: Replication competent HIV between baseline and 48 weeks recombinant human growth hormone administration by QVOA.
2. Secondary Endpoint: Integrated HIV DNA between baseline and 48 weeks recombinant human growth hormone administration by alu-PCR.
3. Secondary Endpoint: Inducible HIV RNA between baseline and 48 weeks recombinant human growth hormone administration by TILDA.

For inclusion in the study, all of the following criteria must be fulfilled:
1. HIV-1 infection and able to provide written consent.
2. Men and women age ≥18 and ≤40 years.
3. Currently on continuous ART for at least 24 months with no change in regimen in 12 weeks prior to study entry. Some modifications of ART doses during the 12 weeks prior to study entry are permitted. In addition, the change in formulation (e.g., from standard formulation to fixed-dose combination) is allowed within 12 weeks prior to study entry. A within class single drug substitution (e.g., switch from tenofovir to abacavir or raltegravir to dolutegravir) is allowed within 12 weeks prior to study entry.
4. CD4+ T-cell count ≥350 cells/mm$^3$ obtained within 30 days prior to study entry.
5. HIV-1 RNA level below the limit of quantification using an FDA-approved assay for at least 24 months prior to study entry and confirmed within 60 days prior to study entry. Single determinations that are between the assay quantification limit and 200 copies/mL are allowed as long as the preceding and subsequent determinations are below the level of quantification.
6. A female, may be eligible to enter and participate in the study if she:
a. is of non-child-bearing potential defined as physically incapable of becoming pregnant with documented tubal ligation, hysterectomy or bilateral oophorectomy or,
b. is of child-bearing potential with a negative pregnancy test at both Screening and Day 1 and agrees to use one of the following methods of contraception to avoid pregnancy:
Complete abstinence from penile-vaginal intercourse from 2 weeks prior to administration of IP, throughout the study, and for at least 2 weeks after discontinuation of all study medications.
Double barrier method (male condom/spermicide, male condom/diaphragm, diaphragm/spermicide); barrier methods must be in use at least 14 days prior to study drug administration.
Any intrauterine device (IUD) with published data showing that the expected failure rate is <1% per year (not all IUDs meet this criterion. IUD must be in use at least 30 days prior to first study drug administration.
Male partner sterilization confirmed prior to the female subject's entry into the study, and this male is the sole partner for that subject; the vasectomy must be completed 3 months prior to first study drug administration or in the alternative that a 0 sperm count will suffice.
Approved hormonal contraception.
Any other method with published data showing that the expected failure rate is <1% per year.
Any contraception method must be used consistently, in accordance with the approved product label and for at least 2 weeks after discontinuation of recombinant human growth hormone.

Subjects will be excluded from this study if they fulfill any of the following exclusion criteria:
1. The following laboratory values obtained at screening:
a. Fasting glucose ≥100 mg/dL
b. Hemoglobin A1c ≥5.7%
c. ALT [serum glutamic pyruvic transaminase (SGPT)]>2 times upper limit of normal (ULN)
d. AST [serum glutamic oxaloacetic transaminase (SGOT)]>2×ULN
e. Estimated creatinine clearance ≤50 mL/min by Cockcroft-Gault
f. Hemoglobin <11.5 g/dL
g. Platelets <100,000/mm$^3$
h. ANC <1000/mm$^3$.
2. Any active or past history of malignancy, except for localized cutaneous Kaposi's sarcoma (fewer than 10 lesions, none of which are larger than 2 cm, and not on active therapy).
3. Prior therapy with growth hormone or tesamorelin during 12 months preceding screening visit.
4. Unstable or untreated hypertension, defined as ≥160/90 mm Hg at the time of the screening visit.

5. History of pancreatitis, carpal tunnel syndrome (unless resolved by surgical release), diabetes mellitus, angina pectoris, coronary artery disease, or any disorder associated with moderate to severe edema (e.g. ascites, nephrotic syndrome, congestive heart failure, lymphedema).
6. Acute or serious illness requiring systemic treatment and/or hospitalization within 90 days prior to study entry.
7. Receipt of antibiotic therapy within 30 days prior to study entry.
8. Chronic hepatitis C infection defined as a positive hepatitis C antibody and positive hepatitis C RNA at any time prior to study entry. Subjects who are positive for hepatitis C antibody but who are HCV RNA negative are permitted in the study.
9. Use of immunomodulators (e.g., interleukins, interferons, cyclosporine), HIV vaccine, systemic cytotoxic chemotherapy, or investigational therapy within 30 days prior to study entry or during study.
10. Known allergy/sensitivity or any hypersensitivity to components of study drug or their formulation.
11. Recent vaccination within 30 days prior to study entry or expected vaccination after screening but before baseline visit.
12. Active drug or alcohol use or dependence that, in the opinion of the site investigator, would interfere with adherence to study requirements.
13. Receive testosterone therapy for hypogonadism unless prior testosterone deficiency is documented.
14. Drug or hormone use as follows:
  a. Men: change in regimen or supraphysiological dose of testosterone (measured by elevated free testosterone above normal levels) within 2 months prior to screening;
  b. anabolic steroids, GH, GH secretagogue, GHRF products or analogs, IGF-1, or IGF binding protein 3 (IGFBP-3) within 6 months prior to screening.
15. Women who are lactating.

Somatropin is a human growth hormone (hGH) produced by recombinant DNA technology. Somatropin has 191 amino acid residues and a molecular weight of 22,125 daltons. Its amino acid sequence and structure are identical to the dominant form of human pituitary growth hormone. Somatropin is produced by a mammalian cell line (mouse C127) that has been modified by the addition of the hGH gene. Somatropin is secreted directly through the cell membrane into the cell-culture medium for collection and purification.

Serostim® is somatropin produced by EMD Serono. Somatropin is a sterile lyophilized powder intended for subcutaneous injection after reconstitution to its liquid form.

Vials of Serostim® [somatropin (rDNA origin) for injection] approved in Canada (DIN number 02239046) contain either 4 mg, 5 mg, 6 mg, or 8.8 mg of somatropin. Only the 5 mg single-use vial will be used for this study.

Each vial contains the following:

| Component | Amount |
|---|---|
| Somatropin | 5 mg |
| Phosphoric acid | 1.2 mg |
| Sodium Hydroxide | 0.7 mg |
| Sucrose | 34.2 mg |

Each Serostim® 5 mg single-use vial is supplied in a combination package with Sterile Water for Injection, USP. The pH is adjusted with sodium hydroxide of phosphoric acid to give a pH of 6.5 to 8.5 after reconstitution. Study medication will be labeled as an "investigational product to be used only by a qualified investigator".

Before reconstitution: Vials of somatropin and diluent should be stored at room temperature, (15°–30° C./59°–86° F.). Expiration dates are stated on product labels. After reconstitution: After reconstitution with Sterile Water for Injection, USP, the reconstituted solution should be administered immediately (within 3 hours). Although not recommended, it may be stored for up to 24 hours at 2-8° C. As there is no preservative in this reconstituted solution, any unused solution should be discarded once the dose is given. Avoid freezing reconstituted vials of somatropin.

All participants will be on combination antiretroviral therapy during the entire duration of the study. If a stable regimen was established at least 2 months prior to screening, testosterone replacement therapy at physiological doses is acceptable during this study as soon as free testosterone levels remain in the normal range.

A subject may be using lipid lowering therapy during participation in this study if he or she has been on a stable dose since at least 2 months prior to screening. A subject may be using antihypertensive therapy during participation in this study if he or she has been on a stable dose since at least 1 month prior to screening and has reached a systolic pressure of ≤160 mm Hg and diastolic pressure of ≤90 mm Hg. Any medications (other than those excluded) that are considered necessary for the subject's welfare and will not interfere with the study drug may be given at the Investigator's discretion.

Clinical Evaluations

Once a candidate for screening has been identified, study details will be carefully discussed with the subject. The subject will be asked to read and sign the approved informed consent form prior to any assessments being performed.

Medical history, documented HIV test results, demographic information, date of initiation of highly active antiretroviral therapy, CD4 count nadir, history of antiretroviral treatment and co-infections: hepatitis A, B, C; syphilis, co-morbidities: diabetes, cardiovascular disease, hypercholesterolemia, bone disease, cancers, AIDS related diagnoses and other medications will be obtained at the screening visit. A complete physical exam, including vital signs will also be performed at the screening visit. A brief physical exam, including vital signs, will be performed as per site local practices at subsequent visits. In addition, the participants will be asked to bring all the recombinant human growth hormone vials (used and unused) with them to each clinic visit. This will allow to measure adherence and ensure that the recommended dose was used.

Blood pressure, weight, and height, medication review and adverse events will be documented in electronic Case Report Forms (eCRFs) at each visit as indicated in Table 2 (Schedule of Events).

Laboratory Evaluations and Specimen Collection

Blood samples will be obtained for clinical laboratory evaluations at each study visit as per routine clinical care (see Clinical Laboratory Tests, below). Subjects should be fasting for at least 8 hours prior to blood work. All clinical laboratory evaluations will be performed at site local laboratories as per local standards of care. When possible, laboratory results will be transferred directly to the main web-based database by the research assistant. If this is not possible, CRF will be available for the site to transcribe the results.

Clinical Laboratory Tests

| Hematology | Serum Chemistry | Serology | Other |
|---|---|---|---|
| Hgb A1C CBC w/ differential CD4 panel | CMP (Comprehensive metabolic panel): Albumin, Alk P'Tase, Total, ALT (SGPT), AST (SGOT), Urea Nitrogen, Calcium, Chloride, C02, Creatinine, glucose, Globulin, Potassium, sodium, Total Bilirubin, Total Protein) Lipid profile (total, HDL/LDL cholesterol, and triglycerides) IGF-1 and IGFBP-3 Quicki index (fasting insulin and glucose) | HCV HBsAg | HIV RNA HCV RNA Pregnancy test |

In addition to the blood collected for the clinical tests described above, blood will be collected to measure changes in the size of the HIV reservoir using 3 different methods described below.

Quantitative viral outgrowth assay (QVOA) is recognized as the gold standard assay for determining the frequency of CD4+ T cells harboring replication competent proviruses, despite its limitations (time consuming, labor-intensive, large blood requirement, expensive, lack of precision, and probably incomplete sensitivity for replication competence). A slightly modified a new protocol (modified QVOA, mQVOA) using the MOLT-4/CCR5 cell line, reducing the time of culture and, by eliminating the low donor-dependent efficiency of prolonged co-culture, this assay enhances sensitivity and precision in patients with the smallest reported reservoirs. The increased sensitivity and speed of the assay is facilitated by 96-well magnetic bead extraction of supernatant (up to 500 μl), which is more efficient than other methods and then direct transfer of all extracted RNA into a 96-well ultrasensitive semi-nested real time RT-PCR with a detection limit of a single copy of HIV RNA. Infected cell frequencies measured with standard QVOA in HIV-infected subjects ART-treated in the chronic phase of the infection is on the order of 0.1 to 1 infectious units per million (IUPM) of CD4 T cell (PMID: 23459007) while mQVOA showed a median of 8.0 [3.2-11.6] IUPM.

We will use 50 million PBMCs for the mQVOA and will enrich PBMCs for total CD4+ T cells, expecting a recovery from 8 to 15 million per sample. Enriched CD4+ T cells will be serially diluted in a 24-well plate coated with anti-CD3 and anti-CD28 monoclonal antibodies. We will perform 2-fold serial dilutions (4 dilutions). The starting concentration will be $1 \times 10^6$ cells/well and three replicates will be performed depending on cell availability. After 2 days of stimulation, $0.2 \times 10^6$ MOLT-4/CCR5 cells will be added to each cell culture well (day 0). Medium will be changed twice a week. Cell culture supernatants will be collected at days 7 and 14 after the addition of MOLT-4/CCR5 cells. Cf-RNA from the supernatant (500 μl) will be extracted using magnetic-beads based technology, and quantified using a semi-nested real time RT-PCR with a detection limit of a single copy of HIV RNA. Extracted viral RNA will be reverse transcribed and subjected to 16 cycles of amplification with the following primers: Forward: 5'-ATG CCA CGT AAG CGA AAC TCT GGG TCT CTC TDG TTA GAC-3' (SEQ ID NO: 1); Reverse: 5'-CCA TCT CTC TCC TTC TAG C-3' (SEQ ID NO: 2). Pre-amplified products will be diluted and subjected to a nested real time PCR for 40 cycles on the Rotor-Gene Q by using the following primers and probes: Forward: 5'-ATG CCA CGT AAG CGA AAC T-3' (SEQ ID NO: 3); Reverse: 5'-CTG AGG GAT CTC TAG TTA CC-3' (SEQ ID NO: 4); Probe: 5'-LC-640-CAC TCA AGG CAA GCT TTA TTG AGG C-BBQ-3 (SEQ ID NO: 5). The number of wells positive for HIV RNA will be determined for each dilution and used to calculate the IUPM using standard maximum likelihood methods.

HIV DNA measurements: We will measure the frequency of total CD4+ T cells harboring total and integrated HIV DNA by using our well-established assays that can detect a single copy of the viral genome in $10^5$ cells [8]. While integrated HIV DNA is present in both latently and productively infected cells, the ratio between total and integrated has been recently shown to reflect residual HIV expression and de-novo reverse transcription [17].

TILDA: We have developed a novel assay that measures the frequency of cells harboring inducible HIV without the requirement of large blood volume [18]. By combining ultrasensitive detection of msRNAs upon stimulation together with a limiting dilution assay, this method allows us to measure a frequency of cells harboring transcriptionally silent—nonetheless inducible—viruses. To our knowledge, TILDA is the only method that allows the measurement of the frequency of cells harboring inducible virus that can be performed with less than a million CD4+ T cells. Therefore, we will be able to measure the magnitude of the reservoir in sorted CD4+ T cells subsets at the leukapheresis time points, but also in total CD4+ T cells at several time points, including those at which the number of cells collected may be limited.

Schedule of Events

Screening (week −7 to −2): Informed consent is obtained, eligibility is determined.

Baseline assessments (week −2): Study subjects will undergo a large blood draw of 120 mL (to determine a first baseline reservoir value by mQVOA).

Recombinant human growth hormone initiation (week 0: Subjects will be sampled (large blood draw, 120 mL) before receiving the first dose of Serostim® (3.0 mg/day) to generate a second baseline value by mQVOA.

Intermediate high dose (week 12): All subjects will receive safety assessment including: symptom directed physical examination and safety labs. A regular blood draw will be performed (30 mL).

Dose reduction (week 24): All enrolled subjects will be sampled (large blood draw for an intermediate reservoir measurement by mQVOA) before starting the reduced dose regimen of recombinant human growth hormone SEROSTIM® (1.5 mg/day).

Intermediate low dose (week 36): All subjects will receive safety assessment including: symptom directed physical examination and safety labs. A regular blood draw will be performed (30 mL).

Study primary endpoint (week 48): Study subjects will undergo a large blood draw (120 mL) to measure the reservoir by mQVOA. Serostim® therapy is stopped. End of the study.

REFERENCES

[1] Palella F J, Jr., Delaney K M, Moorman A C, Loveless M O, Fuhrer J, Satten G A, et al. Declining morbidity and mortality among patients with advanced human immunodeficiency virus infection. HIV Outpatient Study Investigators. N Engl J Med. 1998; 338:853-60.

[2] Durand C M, Blankson J N, Siliciano R F. Developing strategies for HIV-1 eradication. Trends Immunol. 2012; 33:554-62.

[3] Lewin S R, Evans V A, Elliott J H, Spire B, Chomont N. Finding a cure for HIV: will it ever be achievable? J Int AIDS Soc. 2011; 14:4.

[4] Yukl S A, Sinclair E, Somsouk M, Hunt P W, Epling L, Killian M, et al. A comparison of methods for measuring rectal HIV levels suggests that HIV DNA resides in cells other than CD4+ T cells, including myeloid cells. AIDS. 2013.

[5] Chun T W, Stuyver L, Mizell S B, Ehler L A, Mican J A, Baseler M, et al. Presence of an inducible HIV-1 latent reservoir during highly active antiretroviral therapy. Proc Natl Acad Sci USA. 1997; 94:13193-7.

[6] Wong J K, Hezareh M, Gunthard H F, Havlir D V, Ignacio C C, Spina C A, et al. Recovery of replication-competent HIV despite prolonged suppression of plasma viremia. Science. 1997; 278:1291-5.

[7] Finzi D, Hermankova M, Pierson T, Carruth L M, Buck C, Chaisson R E, et al. Identification of a reservoir for HIV-1 in patients on highly active antiretroviral therapy. Science. 1997; 278:1295-300.

[8] Chomont N, El-Far M, Ancuta P, Trautmann L, Procopio F A, Yassine-Diab B, et al. HIV reservoir size and persistence are driven by T cell survival and homeostatic proliferation. Nat Med. 2009; 15:893-900.

[9] Wightman F, Solomon A, Khoury G, Green J A, Gray L, Gorry P R, et al. Both CD31(+) and CD31 naive CD4(+) T cells are persistent HIV type 1-infected reservoirs in individuals receiving antiretroviral therapy. J Infect Dis. 2010; 202:1738-48.

[10] Steinmann G G, Klaus B, Muller-Hermelink H K. The involution of the ageing human thymic epithelium is independent of puberty. A morphometric study. Scandinavian journal of immunology. 1985; 22:563-75.

[11] Napolitano L A, Schmidt D, Gotway M B, Ameli N, Filbert E L, Ng M M, et al. Growth hormone enhances thymic function in HIV-1-infected adults. J Clin Invest. 2008; 118:1085-98.

[12] Napolitano L A, Lo J C, Gotway M B, Mulligan K, Barbour J D, Schmidt D, et al. Increased thymic mass and circulating naive CD4 T cells in HIV-1-infected adults treated with growth hormone. AIDS. 2002; 16:1103-11.

[13] Herasimtschuk A A, Hansen B R, Langkilde A, Moyle G J, Andersen O, Imami N. Low-dose growth hormone for 40 weeks induces HIV-1-specific T cell responses in patients on effective combination anti-retroviral therapy. Clin Exp Immunol. 2013; 173:444-53.

[14] Herasimtschuk A A, Westrop S J, Moyle G J, Downey J S, Imami N. Effects of recombinant human growth hormone on HIV-1-specific T-cell responses, thymic output and proviral DNA in patients on HAART: 48-week follow-up. Journal of immune based therapies and vaccines. 2008; 6:7.

[15] Plana M, Garcia F, Darwich L, Romeu J, Lopez A, Cabrera C, et al. The reconstitution of the thymus in immunosuppressed individuals restores CD4-specific cellular and humoral immune responses. Immunology. 2011; 133:318-28.

[16] Cockerham L R, Siliciano J D, Sinclair E, O'Doherty U, Palmer S, Yukl S A, et al. CD4+ and CD8+ T cell activation are associated with HIV DNA in resting CD4+ T cells. PLoS One. 2014; 9:e110731.

[17] Mexas A M, Graf E H, Pace M J, Yu J J, Papasavvas E, Azzoni L, et al. Concurrent measures of total and integrated HIV DNA monitor reservoirs and ongoing replication in eradication trials. AIDS. 2012; 26:2295-306.

[18] Procopio F A, Fromentin R, Kulpa D A, Brehm J H, Bebin A G, Strain M, et al. A novel assay to measure the magnitude of the inducible viral reservoir in HIV-infected individuals. EBioMedicine. 2015; 2:872-81.

[19] Siliciano J D, Kajdas J, Finzi D, Quinn T C, Chadwick K, Margolick J B, et al. Long-term follow-up studies confirm the stability of the latent reservoir for HIV-1 in resting CD4+ T cells. Nat Med. 2003; 9:727-8.

[20] Spivak A M, Andrade A, Eisele E, Hoh R, Bacchetti P, Bumpus N N, et al. A pilot study assessing the safety and latency-reversing activity of disulfiram in HIV-1-infected adults on antiretroviral therapy. Clin Infect Dis. 2014; 58:883-90.

[21] Product Monograph. Serostim®. EMD Serono Canada, Jun. 22 2012.

---

We claim:

1. A method of treating an HIV-1 infected subject comprising administering a first dose of growth hormone (GH) in an amount of about 2 mg/day to about 5 mg/day to a subject infected with HIV-1 for a first period of time followed by administering a second dose of growth hormone (GH) in an amount of about 3.5 mg/day to about 25 mg/day to said subject for a second period of time, wherein said second dose is an increased dose of GH.

2. The method according to claim 1, wherein administering GH reduces the size of the replication competent HIV reservoir in said subject.

3. The method according to claim 1, wherein the subject is not being treated with an anti-retroviral therapy (ART).

4. The method according to claim 1, wherein the subject has not been treated with an anti-retroviral drug.

5. The method according to claim 1, said method further comprising measuring the size of the replication competent HIV reservoir in said subject after said first dose of GH has been administered to said subject.

6. The method according to claim 1, said method further comprising measuring the size of the replication competent HIV reservoir in said subject prior to administering said first dose of GH to said subject and at the conclusion of said first time period.

7. The method according to claim 1, said method further comprising measuring the size of the replication competent HIV reservoir in said subject prior to administering said first dose of GH to said subject, at the conclusion of said first period of time and at the conclusion of said second time period where said second dose of GH is administered.

8. The method according to claim 1, wherein a size of the replication competent HIV reservoir in said subject is measured prior to administering said first dose of GH to said subject and at multiple time points after the administration of said first dose of GH to the subject and multiple times after the administration of said second dose of GH to the subject.

9. The method according to claim 1, wherein said first and said second doses of GH are co-administered to a subject with one or more anti-retroviral drug (ARD).

10. The method according to claim 9, wherein said one or more anti-retroviral drug is selected from Abacavir; Didanosine; Emtricitabine; Lamivudine; Stavudine; Tenofovir disoproxil fumarate; Tenofovir alafenamide; Zalcitabine; Zidovudine; Delavirdine; Efavirenz; Etravirine; Nevirapine; Rilpivirine; Amprenavir; Atazanavir; Darunavir; Fosamprenavir; Indinavir; Lopinavir/Ritonavir; Nelfinavir; Ritonavir; Saquinavir; Tipranavir; Enfuvirtide; Maraviroc; Dolutegravir; Elvitegravir; Raltegravir; and combinations thereof.

11. The method according to claim 1, wherein said first dose of GH is administered in an amount of about 3 mg/day and said second dose of GH is administered in an amount of about 4.5 to about 15 mg/day.

12. The method according to claim 1, wherein GH is administered subcutaneously, intravenously or intramuscularly.

13. The method according to claim 1, wherein said subject is treated for a first period that ranges between about 2 weeks and about 52 weeks and a second period that ranges between about 2 and about 52 weeks.

14. The method according to claim 13, wherein said first period is a period of about 24 weeks and said second period is a period of about 24 weeks.

15. The method according to claim 1, wherein said subject is in an anti-retroviral therapy (ART) free period.

16. The method according to claim 1, wherein the GH is human growth hormone.

17. The method according to claim 11, wherein said first dose of GH is administered in an amount of about 3 mg/day and said second dose of GH is administered in an amount of about 5 mg/day.

\* \* \* \* \*

UNITED STATES PATENT AND TRADEMARK OFFICE
CERTIFICATE OF CORRECTION

PATENT NO. : 11,707,508 B2
APPLICATION NO. : 16/679425
DATED : July 25, 2023
INVENTOR(S) : Alena Zalutskaya et al.

It is certified that error appears in the above-identified patent and that said Letters Patent is hereby corrected as shown below:

In the Specification

Column 7,
Line 57, "and $\leq$ 40 years" should read --and $<$ 40 years--.

Signed and Sealed this
Twenty-eighth Day of May, 2024

Katherine Kelly Vidal
*Director of the United States Patent and Trademark Office*

SEQUENCE LISTING

```
<160> NUMBER OF SEQ ID NOS: 5

<210> SEQ ID NO 1
<211> LENGTH: 39
<212> TYPE: DNA
<213> ORGANISM: Artificial Sequence
<220> FEATURE:
<223> OTHER INFORMATION: Forward primer

<400> SEQUENCE: 1
atgccacgta agcgaaactc tgggtctctc tdgttagac                           39

<210> SEQ ID NO 2
<211> LENGTH: 19
<212> TYPE: DNA
<213> ORGANISM: Artificial Sequence
<220> FEATURE:
<223> OTHER INFORMATION: Reverse primer

<400> SEQUENCE: 2
ccatctctct ccttctagc                                                 19
```

```
<210> SEQ ID NO 3
<211> LENGTH: 19
<212> TYPE: DNA
<213> ORGANISM: Artificial Sequence
<220> FEATURE:
<223> OTHER INFORMATION: Forward primer

<400> SEQUENCE: 3
atgccacgta agcgaaact                                            19

<210> SEQ ID NO 4
<211> LENGTH: 20
<212> TYPE: DNA
<213> ORGANISM: Artificial Sequence
<220> FEATURE:
<223> OTHER INFORMATION: Reverse primer

<400> SEQUENCE: 4
ctgagggatc tctagttacc                                           20

<210> SEQ ID NO 5
<211> LENGTH: 25
<212> TYPE: DNA
<213> ORGANISM: Artificial Sequence
<220> FEATURE:
<223> OTHER INFORMATION: probe

<400> SEQUENCE: 5
cactcaaggc aagctttatt gaggc                                     25
```